(12) United States Patent
Silverman et al.

(10) Patent No.: US 8,093,185 B2
(45) Date of Patent: Jan. 10, 2012

(54) ENHANCEMENT OF PLANT GROWTH

(75) Inventors: Franklin Paul Silverman, Highland Park, IL (US); Dale O. Wilson, Jr., Round Lake Beach, IL (US); Jennifer C. Kochan, Palatine, IL (US); Nicole Higgs, Racine, WI (US); Peter D. Petracek, Grayslake, IL (US); Prem Warrior, Green Oaks, IL (US); Karen S. Arthur, Plano, TX (US)

(73) Assignees: Valent BioSciences Corporation, Libertyville, IL (US); Valent U.S.A. Corporation, Walnut Creek, CA (US)

( * ) Notice: Subject to any disclaimer, the term of this patent is extended or adjusted under 35 U.S.C. 154(b) by 469 days.

(21) Appl. No.: 12/257,475

(22) Filed: Oct. 24, 2008

(65) Prior Publication Data

US 2009/0111698 A1 Apr. 30, 2009

Related U.S. Application Data

(60) Provisional application No. 61/000,366, filed on Oct. 25, 2007.

(51) Int. Cl.
*A01N 37/10* (2006.01)
*A01N 43/00* (2006.01)
*A01N 43/48* (2006.01)
*A01N 43/78* (2006.01)
*A01N 25/32* (2006.01)

(52) U.S. Cl. ........ 504/321; 504/103; 514/341; 514/365; 514/471; 424/405

(58) Field of Classification Search ............... 504/321, 504/103, 341, 365, 471; 424/405
See application file for complete search history.

(56) References Cited

U.S. PATENT DOCUMENTS

| 3,334,991 A | 8/1967 | Hageman et al. |
| 6,753,296 B1 * | 6/2004 | Senn et al. ............ 504/221 |
| 2006/0270559 A1 | 11/2006 | Maekawa et al. |
| 2007/0129442 A1 | 6/2007 | Deyn et al. |

OTHER PUBLICATIONS

Itagaki, M., Biological Activities and Structure-Activity Relationship of Substitution Compounds of N-[2-(3-indoyly)ethyl]succinamic acid and N-[2-(1-naphthyl)ethyl]succinamic acid, derived from a new category of root-promoting substances, N-(phenethyl)succinamic acid analogs, 2003, Plant and Soil, vol. 255, pp. 67-75.*

Itagaki et al., "Biological Activities and Structure-activity relationship substitution compounds of N-[2-3-indolyl)ethyl]succinamaic acid and N-[2-(1-naphthyl)ethyl] succinamic acid, derived from a new category of root-promoting substances, N-(phenethyl) succinamic acid analogs" Plant and Soil 255: 67-75, Aug. 2003, Abstract.

* cited by examiner

*Primary Examiner* — Johann Richter
*Assistant Examiner* — Andriae M Holt
(74) *Attorney, Agent, or Firm* — Wood, Phillips, Katz, Clark & Mortimer

(57) ABSTRACT

Treatment with N-(2-phenylethyl)succinamic acid or its salts protects against inhibition of growth by a neonicotinoid compound applied as a seed treatment or applied directly on or near the root zone of the seedling.

12 Claims, No Drawings

ENHANCEMENT OF PLANT GROWTH

FIELD OF THE INVENTION

The present invention is directed to improving plant growth and consequently yield using N-(2-phenylethyl)succinamic acid (PESA) or its salt, in the presence of a neonicotinoid compound. This is accomplished using a combination treatment of PESA or its salt and a neonicotinoid compound applied as a seed treatment or applied directly to or near the root zone of a seedling or growing plant.

BACKGROUND OF THE INVENTION

Seeds are commonly treated with pesticides to control insects, nematodes, and disease organisms such as fungi and bacteria. Neonicotinoid compounds are commonly active ingredients of insecticides used for treating seeds. Among the commercially available neonicotinoid compounds are clothianidin (tradename Poncho®), imidacloprid (tradename Gaucho®), thiamethoxam (tradename Cruiser®), and dinotefuran (tradename Safari®). N-(2-phenylethyl)succinamic acid is root growth promoter (Soejima, H., et al., Plant Cell Physiol., 2000. 41: p. 197; Itagaki, M., et al., 6th Symposium of the International Society of Root Research, 2001. C1-8; Itagaki, M., et al., Plant Soil, 2003. 255: p. 67-75). Effects of combinations of neonicotinoid compounds and PESA or its salts on plant growth have not been previously examined.

SUMMARY OF THE INVENTION

The present invention is directed to improving plant growth and consequently yield using PESA or its salt in the presence of a neonicotinoid compound. This is accomplished by using a combination treatment of PESA or its salt and at least one neonicotinoid compound applied as a seed treatment or applied directly to or the root zone of a seedling or growing plant. Alternatively, the combination treatment of the present invention may be applied to the shoots or leaves of the plant. This invention permits the use of higher rates of neonicotinoid compounds. The combination treatment can be performed by applying a composition comprising PESA or its salt and a neonicotinoid compound as well as by applying PESA or its salt and a neonicotinoid compound separately.

DETAILED DESCRIPTION OF THE INVENTION

Seed treatments are used on a large variety of crops to control pests. Seed treatments are commonly used to ensure uniform stand establishment by protecting against diseases and insects. Systemic seed treatments may provide an alternative to foliar sprays of fungicides or insecticides for certain early season diseases and insects.

Conventional means of coating may be used for carrying out the coating of the seed treatment formulation. Various coating machines and methods are available to one skilled in the art. Well known techniques include the use of drum coaters and fluidized bed techniques. Other methods, such as spouted beds, may also be useful.

Film-forming compositions for enveloping seeds are well known in the art, and a film overcoat can be optionally applied to the coated seeds of the present invention. The film overcoat protects the coating layers and may allow easy identification of the treated seeds. In general, additives are dissolved or dispersed in a liquid adhesive, usually a polymer, into which or with which seeds are dipped or sprayed before drying. Alternatively, a powder adhesive can be used. Various materials are suitable for overcoats including but not limited to methyl cellulose, hydroxypropylmethylcellulose, dextrin, gums, waxes, vegetable or paraffin oils; water soluble or water disperse polysaccharides and their derivatives, such as alginates, starch, and cellulose; and synthetic polymers such as polyethylene oxide, polyvinyl alcohol, polyvinylpyrrolidone, and their copolymers, related polymers, and mixtures of these.

Further materials may be added to the overcoat optionally including plasticizers, colorants, brighteners and surface active agents, such as dispersants, emulsifiers and flow agents, including, for example, calcium stearate, talc and vermiculite. Additionally, pesticides, such as fungicides, may be added to the film coat. However, it has been observed that fungicides initially added to the seed provide better results than when added with the overcoat. Fluidized bed and drum film coating techniques described above can also be employed for film coating.

Many seed treatment materials are also available for on-farm use wherein liquid or dry formulations are applied to seed as it passes through an auger from the transport bin or truck to planter boxes. These formulations offer a convenient way to apply seed treatment onto bulk seed right before planting. Conventional dry treatments generally are formulated with talc or graphite that adhere the treatment chemical to the seed. Conventional liquid hopper-box treatments generally are made available as fast-drying formulations. In any case, good seed coverage is required for maximum benefit from any seed treatment formulation.

For purposes of this application, PESA is defined as N-(2-phenylethyl)succinamic acid which can be prepared by the method described in WO 99/45774. Clothianidin is defined as (E)-1-(2-chloro-1,3-thiazol-5-ylmethyl)-3-methyl-2-nitroguanidine, imidacloprid is defined as (EZ)-1-(6-chloro-3-pyridylmethyl)-N-nitroimidazolidin-2-ylideneamine, thiamethoxam is defined as (EZ)-3-(2-chloro-1,3-thiazol-5-ylmethyl)-5-methyl-1,3,5-oxadiazinan-4-ylidene(nitro) amine, and dinotefuran is defined as (EZ)-(RS)-1-methyl-2-nitro-3-(tetrahydro-3-furylmethyl)guanidine.

Suitable neonicotinoid compounds include but are not limited to, clothianidin, imidacloprid, thiamethoxam, dinotefuran, acetamiprid, nytenpyram and thiacloprid.

Suitable salts of PESA include, but are not limited to the calcium, magnesium, potassium, sodium or ammonium salts. The presently preferred salt is the sodium salt. Ammonium salts include the salts formed by neutralization of the acid by ammonia itself or by amines bearing one, two or three lower alkyl groups and/or hydroxy-lower alkyl groups, wherein lower alkyl is defined as consisting of one to four carbon atoms arranged in a straight or branched chain. Suitable amines include, but are not limited to trimethylamine, isopropylamine, ethanolamine, dimethylethanolamine, diethanolamine or triethanolamine.

The phrase "the root zone of a seedling or plant" means a zone where the root is spread underground, generally a zone from 1 to 100 cm of radius from the center of the seedling or growing plant.

Preparation of PESA Salt

Salts of PESA were produced by stirring the free acid in water and adding an equimolar amount of an appropriate base to the solution. In the case of the PESA sodium salt, sodium hydroxide is used. This method allows for the production of salt solutions ranging in concentration from 0.01% to at least 40%.

Use of PESA or PESA Salts

The concentration of PESA or PESA salt is preferably in the range of 0.021 to 20.1 percent by volume of the composition, and the concentration of the neonicotinoid compound is preferably in the range of 0.3 to 30.0 percent by weight of the composition.

The weight ratio of the PESA or PESA salt to the neonicotinoid compound in the compositions of the present invention is 1:40 to 1:1, preferably 1:20 to 1:2, and most preferably 1:10 to 1:3.

Aqueous compositions to be utilized in the present invention generally contain from at least about 2% to about 10% by weight of a surface-active agent. In one embodiment, the aqueous compositions contain from about 3% to about 7% by weight of a surface-active agent.

The aqueous composition generally also comprises an anionic surfactant. In general, the anionic surfactant may be any known anionic surfactant in the art. Suitable anionic surfactants are in general oligomers and polymers, as well as polycondensates, which contain a sufficient number of anionic groups to ensure their water-solubility. Suitable anionic surfactants include alcohol sulfates, alcohol ether sulfates, alkylaryl ether sulfates, alkylaryl sulfonates such as alkylbenzene sulfonates and alkylnaphthalene sulfonates and salts thereof, alkyl sulfonates, mono- or di-phosphate esters of polyalkoxylated alkyl alcohols or alkylphenols, mono- or di-sulfosuccinate esters of $C_{12}$-$C_{15}$ alkanols or polyalkoxylated $C_{12}$-$C_{15}$ alkanols, alcohol ether carboxylates, phenolic ether carboxylates, polybasic acid esters of ethoxylated polyoxyalkylene glycols consisting of oxybutylene or the residue of tetrahydrofuran, sulfoalkylamides and salts thereof such as N-methyl-N-oleoyltaurate Na salt, polyoxyalkylene alkylphenol carboxylates, polyoxyalkylene alcohol carboxylates alkyl polyglycoside/alkenyl succinic anhydride condensation products, alkyl ester sulfates, napthalene sulfonates, naphthalene formaldehyde condensates, alkyl sulfonamides, sulfonated aliphatic polyesters, sulfate esters of styrylphenyl alkoxylates, and sulfonate esters of styrylphenyl alkoxylates and their corresponding sodium, potassium, calcium, magnesium, zinc, ammonium, alkylammonium, diethanolammonium, or triethanolammonium salts, salts of ligninsulfonic acid such as the sodium, potassium, magnesium, calcium or ammonium salt, polyarylphenol polyalkoxyether sulfates and polyarylphenol polyalkoxyether phosphates, and sulfated alkyl phenol ethoxylates and phosphated alkyl phenol ethoxylates.

The aqueous composition generally also includes at least one polymer selected from water-soluble and water-dispersible film-forming polymers. Suitable polymers have an average molecular weight of at least about 1,000 up to about 100,000; more specifically at least about 5,000, up to about 100,000. The aqueous compositions generally contain from about 0.01% to about 10%, preferably about 0.05 to about 8%, more preferably about 0.1% to about 5%, especially about 0.5% to about 4% by weight of the composition of polymer. In a specific embodiment, the compositions contain from about 1.0% up to about 4% by weight of a film-forming polymer. In another embodiment, the compositions contain about 0.05 to 1% by weight of the film-forming polymer.

Suitable polymers include alkyleneoxide random and block copolymers such as ethylene oxide-propylene oxide block copolymers (EO/PO block copolymers), including both EO-PO-EO and PO-EO-PO block copolymers; ethylene oxide-butylene oxide random and block copolymers, $C_{2-6}$ alkyl adducts of ethylene oxide-propylene oxide random and block copolymers, $C_{2-6}$ alkyl adducts of ethylene oxide-butylene oxide random and block copolymers, polyoxyethylene-polyoxypropylene monoalkylethers, such as methyl ether, ethyl ether, propyl ether, butyl ether or mixtures thereof; vinylacetate/vinylpyrrolidone copolymers; alkylated vinylpyrrolidone copolymers; polyvinylpyrrolidone; and polyalkyleneglycol, including the polypropylene glycols and polyethylene glycols.

The aqueous composition generally also comprises, from at least about 3 to about 25% of at least one antifreeze agent. In one embodiment, the amount of an antifreeze agent is from about 6% to about 20% by weight.

Specific examples of suitable antifreezes include ethylene glycol, 1,2-propylene glycol, 1,3-propylene glycol, 1,2-butanediol, 1,3-butanediol, 1,4-butanediol, 1,4-pentanediol, 3-methyl-1,5-pentanediol, 2,3-dimethyl-2,3-butanediol, trimethylol propane, mannitol, sorbitol, glycerol, pentaerythritol, 1,4-cyclohexanedimethanol, xylenol, bisphenols such as bisphenol A or the like. In addition, ether alcohols such as diethylene glycol, triethylene glycol, tetraethylene glycol, polyoxyethylene or polyoxypropylene glycols of molecular weight up to about 4000, diethylene glycol monomethylether, diethylene glycol monoethylether, triethylene glycol monomethylether, butoxyethanol, butylene glycol monobutylether, dipentaerythritol, tripentaerythritol, tetrapentaerythritol, diglycerol, triglycerol, tetraglycerol, pentaglycerol, hexaglycerol, heptaglycerol, octaglycerol and the like.

Additionally, a coloring agent, such as a dye or pigment, may be included in the seed coating so that an observer can immediately determine that the seeds are treated. The dye is also useful to indicate to the user the degree of uniformity of the coating applied.

The formulations of the present invention contain sufficient water to bring the total weight to 100%.

The formulations of the present invention are applied to seeds or to the root zone at rates of 1 to 2000 grams active ingredients/acre and preferably 5 to 200 grams active ingredients/acre.

A formulation comprising PESA or its salt as an active ingredient and another formulation comprising a neonicotinoid compound as an active ingredient can be applied to seeds or to or the root zone separately. The total application rate of the formulations is 1 to 2000 grams active ingredients/acre and preferably 5 to 200 grams active ingredients/acre. The weight ratio of the PESA or PESA salt to the neonicotinoid compound applied is 1:40 to 1:1, preferably 1:20 to 1:2, and most preferably 1:10 to 1:3.

Especially suitable target crops comprise cereals (such as wheat, barley, rye, oats, rice), maize, sugar beet, cotton, millet, sorghum, sunflower, bean, peas, oil plants (such as canola, rape, and soybean), potato, tomato, eggplant, pepper, and other vegetables (such as cucurbits and cole crops) and spices, as well as woody perennials, ornamental shrubs, fruit trees, grapevines, fruits (such as strawberries and blueberries), turf, grass, pastures and flowers.

Suitable target crops also include non-transgenic or transgenic crop plants of the foregoing crops. The transgenic crop plants useful according to the invention are plants, or propagation material thereof, which are transformed by recombinant DNA technology in order to incorporate certain desired traits such as, but not limited to, synthesis of selectively acting toxins from toxin-producing invertebrates, especially of the phylum Arthropoda; from *Bacillus thuringiensis* strains; from plants, such as lectins; or in the alternative, capable of expressing a herbicidal or fungicidal resistance.

The compositions are particularly suited for applications on plant propagation material. The latter term embraces seeds of all kinds (e.g. fruit, tubers, or grains), cuttings, cut shoots and the like. The preferred field of application is the treatment of all kinds of seeds as specified in the target crops above, and in particular, the seed treatment of canola, maize, cereals, soybeans and other legumes and crops.

Procedure for Treating Samples of Seed in the Laboratory

Seed was sieved with a screen of hole size appropriate to remove broken seeds and small trash. Cracked or otherwise damaged seeds were removed. The seed was well mixed, and 50 g samples were weighed into small plastic trays. Seed treatment slurries were made by adding measured amounts of the active ingredients to sufficient water to bring them up to a standard volume, typically 2 ml. A fungicide (Maxim XL; Syngenta Agricultural Products, Greensboro, N.C.), a polymeric binder (CF-Clear; Becker-Underwood, Ames, Iowa), and a colorant (Color Coat Red; Becker-Underwood, Ames, Iowa) were also included in the slurry at label rates. A small aliquot of this slurry was applied to the seed using the Hege 11 coater (Wintersteiger, Salt Lake City, Utah) with a six-inch bowl. The slurry was deposited drop-wise on the spinning disk atomizer using a syringe.

Pouch Assay

Seeds were placed in germination pouches consisting of germination paper hydrated with sterile water that was an insert in a gas-permeable 16×14 cm plastic pouch (CYG Pouch; Mega International, St. Paul, Minn.). In these examples, in pouch solution evaluation, clothianidin and PESA sodium salt were added to the sterile water in the pouch. Alternatively, imidacloprid or dinotefuran and PESA sodium salt were added to the sterile water in the pouch. The pouches were arranged in a completely randomized block design in growth racks and placed in 19-liter polycarbonate food storage containers (Rubbermaid Commercial Products, Winchester, Va.). The scaled containers were held in an upright growth cabinet maintained at 25 C with a 12 hour light: 12 hour dark photoperiod. After 6 days, the containers were removed from the growth cabinet, and the lengths of the roots and shoot were measured.

Field Studies

For the field studies, the seed was treated with a seed treatment formulation containing clothianidin. The rate of clothianidin was dependent on the crop species. The seed treatment formulations were amended with the appropriate concentrations of either PESA or the sodium salt of PESA.

Crops were planted and grown under standard agricultural practices, and evaluated at the times indicated.

The following examples are intended to illustrate the present invention and to teach one of ordinary skill in the art how to make and use the invention. They are not intended to be limiting in any way.

EXAMPLES

Example 1

Preparation Example

The following representative formulations in which all percentages are weight percentages may be prepared:

Formulation A (in-bottle formulation of PESA salt and neonicotinoid):

PESA Sodium Salt: 5%
Clothianidin: 30%
Tween 20: 5%
N-methylpyrrolidone 20%
Polyvinyl acetate: 2%
Potassium Sorbate: 1%
Water 37%.

Clothianidin may be mixed with N-methylpyrrolidone and Tween 20 at room temperature to produce a concentrate. Separately, the sodium salt of PESA may be mixed with polyvinyl acetate and potassium sorbate in water to produce an aqueous mixture. While stirring the aqueous mixture, the clothianidin-containing concentrate may be added. This will produce a formulation that may be used for the treatment of seeds, plants, or applied to the root zone of seedlings or plants.

Formulation B (in-bottle formulation of PESA and neonicotinoid):

Milled PESA: 5%
Clothianidin: 30%
Tween 20: 5%
N-methylpyrrolidone 16%
Polyvinyl acetate: 2%
Potassium Sorbate: 1%
Lignin Sulfate: 1%
Water: 40%.

Clothianidin may be mixed with N-methylpyrrolidone and Tween 20 at room temperature to produce a concentrate. Separately, PESA may be mixed with lignin sulfate, Tween 20 and water and milled in a wet milling machine for 1-2 hours in order to reduce particle size. The milled PESA may be mixed with polyvinyl acetate and potassium sorbate to produce an aqueous mixture. While stirring the aqueous mixture, the clothianidin-containing concentrate may be added. This will produce a formulation that may be used for the treatment of seeds, plants, or applied to the root zone of seedlings or plants.

Formulation C (separate bottle formulations of PESA salt and neonicotinoid):

Bottle 1:
PESA Sodium Salt: 10%
Tween20: 10%
Polyvinyl acetate: 2%
Potassium Sorbate: 1%
Water: 77%.

The sodium salt of PESA may be mixed with polyvinyl acetate, Tween 20 and potassium sorbate in water to produce an aqueous mixture.

Bottle 2:
Clothianidin 60%
Tween 20: 5%
N-methylpyrrolidone: 35%.

Clothianidin may be mixed with N-methylpyrrolidone and Tween 20 at room temperature to produce a concentrate.

While stirring the aqueous mixture in bottle 1, the clothianidin-containing concentrate in bottle 2 may be added. This will produce a formulation that may be used for the treatment of seeds, plants, or applied to the root zone of seedlings or plants.

Formulation D (separate bottle formulations of PESA and neonicotinoid):

Bottle 1:
Milled PESA: 10%
Tween 20: 10%
Lignin Sulfate 1%
Polyvinyl acetate: 2%
Potassium Sorbate: 1%
Water: 76%.

PESA may be mixed with lignin sulfate, Tween 20 and water and milled in a wet milling machine for 1-2 hours in order to reduce particle size. The milled PESA may be mixed with polyvinyl acetate and potassium sorbate to produce an aqueous mixture.

Bottle 2:
Clothianidin 60%
Tween 20: 5%
N-methylpyrrolidone: 35%.

Clothianidin may be mixed with N-methylpyrrolidone and Tween 20 at room temperature to produce a concentrate.

While stirring the aqueous mixture in bottle 1, the clothianidin-containing concentrate in bottle 2 may be added. This will produce a formulation that may be used for the treatment of seeds, plants, or applied to the root zone of seedlings or plants.

Example 2

Seed treatment with clothianidin alone with 182 or 364 g/100 pounds of seed reduced cotton root length (Table 1). A seed treatment combination of clothianidin with PESA salt increased the root length of cotton. For cotton treated with the lower rate of 10 grams PESA salt/100 pounds of seed combined with 182 or 364 grams clothianidin/100 pounds of seed, root length was greater than control, PESA salt alone, or clothianidin alone at the respective rates. For cotton treated with the higher rate of 25 grams PESA salt/100 pounds of seed combined with 182 or 364 grams clothianidin/100 pounds of seed, root length was greater than control, or clothianidin alone at the respective rates.

This indicates that PESA salt safened cotton against clothianidin-induced root growth inhibition.

TABLE 1

Effect of PESA salt and clothianidin seed treatments on root length (cm) of cotton.

| PESA salt (grams/100 pounds of seed) | Clothianidin (grams/100 pounds of seed) | | |
|---|---|---|---|
| | 0 | 182 | 364 |
| 0 | 9.6 | 7.8 | 7.9 |
| 10 | 8.8 | 9.0 | 9.1 |
| 25 | 10.6 | 10.1 | 9.8 | n = 7 replicate pouches of 3 plants/pouch per treatment.

Treatment with clothianidin alone, PESA salt, and combinations of clothianidin with PESA salt increased cotton shoot length (Table 2).

TABLE 2

Effect of PESA salt and clothianidin seed treatments on shoot length (cm) of cotton.

| PESA salt (grams/100 pounds of seed) | Clothianidin (grams/100 pounds of seed) | | |
|---|---|---|---|
| | 0 | 182 | 364 |
| 0 | 3.7 | 4.1 | 4.2 |
| 10 | 4.3 | 4.3 | 4.2 |
| 25 | 4.3 | 4.0 | 4.2 | n = 7 replicate pouches of 3 plants/pouch per treatment.

Example 3

In continuous exposure pouch studies, treatment with clothianidin alone decreased the length of the root (Table 3). PESA salt increased root length in a dose-dependent manner. The combination of clothianidin and 100 mg/liter PESA salt increased root length compared to the untreated control.

This indicates that PESA salt safened cotton against clothianidin-induced root growth inhibition.

TABLE 3

Effect of PESA salt and clothianidin on root length (cm) of cotton.

| PESA salt (mg/liter) | Clothianidin (mg/liter) | |
|---|---|---|
| | 0 | 1000 |
| 0 | 11.4 | 8.9 |
| 10 | 14.2 | 10.0 |
| 30 | 15.3 | 10.4 |
| 100 | 16.2 | 12.5 | n = 8 replicate pouches of 3 seedlings/pouch per treatment.

In continuous exposure pouch studies, cotton shoot length was not affected by clothianidin alone (Table 4). Shoot length of the treatment with the 300 mg/liter (the highest rate) of PESA salt alone was reduced, but was not affected by the combination of clothianidin with 300 mg/liter PESA salt.

TABLE 4

Effect of PESA salt and clothianidin on shoot length (cm) of cotton

| PESA salt (mg/liter) | Clothianidin (mg/liter) | |
|---|---|---|
| | 0 | 1000 |
| 0 | 6.1 | 6.1 |
| 10 | 6.3 | 6.2 |
| 30 | 6.1 | 6.0 |
| 100 | 6.0 | 6.1 |
| 300 | 5.4 | 5.8 | n = 8 replicate pouches of 3 seedlings/pouch per treatment.

Example 4

In a continuous exposure pouch study, treatment with imidacloprid (1000 mg/liter) alone decreased root length (Table 5). Root lengths of combination treatments of imidacloprid with PESA salt were greater than root length of the imidacloprid alone treatment. Root lengths of the control and combination treatment of imidacloprid with 100 mg/liter PESA salt were similar.

This indicates that PESA salt safened cotton against imidacloprid-induced root growth inhibition.

TABLE 5

Effect of PESA salt and imidacloprid on root length (cm) of cotton

| PESA salt (mg/liter) | Imidacloprid (mg/liter) | |
|---|---|---|
| | 0 | 1000 |
| 0 | 13.3 | 7.7 |
| 10 | 14.6 | 9.4 |
| 30 | 16.9 | 12.1 |
| 100 | 16.5 | 13.6 |
| 300 | 11.9 | 12.0 | n = 8 replicate pouches of 3 seedlings/pouch per treatment.

Cotton shoot length was not affected by imidacloprid alone (Table 6). Shoot length of the combination treatment of imidacloprid with highest rate (300 mg/liter) of PESA salt was reduced.

TABLE 6

Effect of PESA salt and imidacloprid on shoot length (cm) of cotton

| PESA salt (mg/liter) | Imidacloprid (mg/liter) | |
| --- | --- | --- |
| | 0 | 1000 |
| 0 | 6.2 | 6.0 |
| 10 | 6.2 | 5.8 |
| 30 | 6.0 | 5.8 |
| 100 | 6.0 | 5.8 |
| 300 | 5.7 | 5.4 | n = 8 replicate pouches of 3 seedlings/pouch per treatment.

Example 5

In a continuous exposure pouch study with PESA salt solutions, seed treatment with imidacloprid alone decreased the root length in a dose-dependent manner (Table 7). Inclusion of PESA salt (50 mg/liter) in the pouch increased the root length of the imidacloprid-treated seed. Root lengths of the control and combination treatment of 200 grams imidacloprid/100 pounds of seed with 50 mg/liter PESA salt were similar.

This indicates that PESA salt safened rice against imidacloprid-induced root growth inhibition.

TABLE 7

Effect of PESA salt and imidacloprid on root length (cm) of rice

| Imidacloprid (grams/100 pounds of seed) | PESA salt (mg/liter) | |
| --- | --- | --- |
| | 0 | 50 |
| 0 | 10.7 | 12.0 |
| 200 | 9.6 | 10.5 |
| 400 | 8.9 | 9.8 |
| 800 | 8.3 | 8.7 | n = 8 replicate pouches of 3 seedlings/pouch per treatment.

Rice shoot lengths for imidacloprid alone and in combination with PESA salt were similar (Table 8).

TABLE 8

Effect of PESA salt and imidacloprid on shoot length (cm) of rice

| Imidacloprid (grams/100 pounds of seed) | PESA salt (mg/liter) | |
| --- | --- | --- |
| | 0 | 50 |
| 0 | 3.3 | 3.6 |
| 200 | 3.6 | 3.7 |
| 400 | 3.3 | 3.1 |
| 800 | 3.6 | 2.9 | n = 8 replicate pouches of 3 seedlings/pouch per treatment.

Example 6

The sodium salt of PESA was prepared as described above, and was used in seed treatment either alone or in the presence of clothianidin. Soybean seed was treated with 0 or 50 grams of clothianidin/100 kg (220 pound) of seed and with 0, 22, 55, or 137.5 grams PESA salt/100 kg seed. Clothianidin alone reduced plant height as compared to the control. Plant height of seeds treated with clothianidin and PESA salt at 22 and 55 grams/100 kg was greater than that of the clothianidin alone (Table 9).

This indicates that PESA salt safened soybean against clothianidin-induced root growth inhibition.

TABLE 9

Effect of PESA salt and clothianidin seed treatment on average plant height (inches) of soybean at 66 days after planting near Indianapolis, IN, USA

| Clothianidin (g/100 kg seed) | Sodium salt of PESA (g/100 kg/seed) | Plant Height (inches) |
| --- | --- | --- |
| 0 | 0 | 23.8 |
| 50 | 0 | 21.6 |
| 50 | 22 | 24.8 |
| 50 | 55 | 24.1 |
| 50 | 137.5 | 22.1 |
| 0 | 22 | 23.8 |
| 0 | 55 | 23.5 |
| 0 | 137.5 | 23.2 |

Example 7

The sodium salt of PESA was prepared as described above, and was used in seed treatment either alone or in the presence of clothianidin. Sorghum seed was treated with 0 or 200 grams of clothianidin/100 kg (220 pound) of seed and with 0, 22, 55, or 137.5 grams PESA salt/100 kg seed. Clothianidin alone reduced root dry weight as compared to the control. Root dry weight from seeds treated with clothianidin and PESA salt at 22 and 55 grams/100 kg had greater root dry weight than the clothianidin alone (Table 10).

This indicates that PESA salt safened sorghum against clothianidin-induced root growth inhibition.

TABLE 10

Effect of PESA salt and clothianidin seed treatment on root dry weight of a sample of 10 sorghum plants at 73 days after planting near Indianapolis, IN, USA

| Clothianidin (g/100 kg seed) | Sodium salt of PESA (g/100 kg/seed) | Root Dry Weight (grams) |
| --- | --- | --- |
| 0 | 0 | 148.5 |
| 200 | 0 | 108.7 |
| 200 | 22 | 124.1 |
| 200 | 55 | 143.4 |
| 200 | 137.5 | 136.0 |
| 0 | 22 | 183.5 |
| 0 | 55 | 146.5 |
| 0 | 137.5 | 141.6 |

Example 8

The sodium salt of PESA was prepared as described above, and was used in seed treatment either alone or in the presence of clothianidin. Canola (*Brassica napus*) seed was treated with 0 or 400 grams of clothianidin/100 kg (220 pound) of seed and with 0, 22, 55, or 137.5 grams PESA salt/100 kg seed. Clothianidin alone reduced plant vigor as compared to the control. Plant vigor from seeds treated with clothianidin and PESA salt at all rates had greater plant vigor than the clothianidin alone (Table 11).

This indicates that PESA salt safened canola against clothianidin-induced vigor reduction.

TABLE 11

Effect of PESA salt and clothianidin seed treatment on vigor rating (1 = low and 5 = high) of canola plants at 19 days after planting near Portage la Prairie, Manitoba, Canada.

| Clothianidin (g/100 kg seed) | Sodium salt of PESA (g/100 kg/seed) | Vigor (1-5) |
|---|---|---|
| 0 | 0 | 3.8 |
| 400 | 0 | 2.5 |
| 400 | 22 | 3 |
| 400 | 55 | 3 |
| 400 | 137.5 | 3 |
| 0 | 22 | 3.8 |
| 0 | 55 | 4 |
| 0 | 137.5 | 4 |

Example 9

The PESA or the sodium salt of PESA was prepared as described above, and was used in seed treatment either alone or in the presence of clothianidin. Maize (*Zea mays*) seed was treated with 0 or 0.25 milligrams of clothianidin/seed and with 0, 22, 55, or 137.5 grams PESA salt/100 kg seed. Clothianidin alone reduced plant vigor as compared to the control. Plant vigor from seeds treated with clothianidin and PESA or the sodium salt of PESA had greater plant vigor than the clothianidin alone (Table 12).

This indicates that PESA or the sodium salt of PESA safened maize against clothianidin-induced vigor reduction.

TABLE 12

Effect of PESA or the sodium salt of PESA and clothianidin seed treatment on vigor rating of maize plants at 27 days after planting near Whitewater, Wisconsin.

| Clothianidin (mg/seed) | PESA (g/100 kg/seed) | Vigor (1-5) |
|---|---|---|
| 0 | 0 | 3.6 |
| 0.25 | 0 | 3.1 |
| 0.25 | 22 (Sodium salt) | 3.6 |
| 0.25 | 55 (Sodium salt) | 3.6 |
| 0.25 | 137.5 (Sodium salt) | 3.2 |
| 0.25 | 55 | 3.6 |
| 0 | 22 (Sodium salt) | 3.8 |
| 0 | 55 (Sodium salt) | 3.5 |
| 0 | 137.5 (Sodium salt) | 3.4 |

The invention claimed is:

1. A composition for enhancing plant growth comprising N-(2-phenylethyl) succinamic acid (PESA) or its salt and at least one neonicotinoid compound selected from the group consisting of clothianidin and imidacloprid, wherein the ratio of PESA to neonicotinoid compound is from 1:3.3 to 1:100.

2. A composition as in claim 1 where the N-(2-phenylethyl) succinamic salt is the sodium salt.

3. A composition as in claim 1 where the neonicotinoid compound is clothianidin.

4. A composition as in claim 1 where the neonicotinoid compound is imidacloprid.

5. A composition as in claim 2 wherein the concentration of the N-(2-phenylethyl)succinamic acid salt is from 0.021 percent to 20.1 percent by volume of the composition.

6. A composition as in claim 1 wherein the concentration of the neonicotinoid compound is from 0.3 percent to 30 percent by weight of the composition.

7. A method of enhancing the growth of plants by applying an effective amount of N-(2-phenylethyl) succinamic acid (PESA) or its salt and at least one neonicotinoid compound selected from the group consisting of clothianidin and imidacloprid to seeds or the root zone of seedlings or plants; and wherein the ratio of PESA to neonicotinoid compound is from 1:3.3 to 1:100.

8. The method of claim 7 where the N-(2-phenylethyl) succinamic acid or its salt and the neonicotinoid compound are applied to seeds.

9. A method of enhancing the growth of plants by applying an effective amount of the composition of claim 1 to seeds or the root zone of seedlings or plants.

10. The method of claim 7 where the composition is applied to seeds.

11. A method for safening plants by applying an effective amount of N-(2-phenylethyl) succinamic acid (PESA) or its salt and at least one neonicotinoid compound selected from the group consisting of clothianidin and imidacloprid to seeds or the root zone of seedlings or plants; and wherein the ratio of PESA to neonicotinoid is from 1:3.3 to 1:100.

12. A composition as in claim 1 where the ratio of PESA to neonicotinoid is 1:6.

* * * * *